United States Patent [19]

Matsumura et al.

[11] Patent Number: 5,503,166
[45] Date of Patent: Apr. 2, 1996

[54] DILUTION MONITORING SYSTEM FOR FILTER CIGARETTES

[75] Inventors: Takeshi Matsumura; Fumio Kubo; Mikio Komori; Takehiro Suzuki, all of Tokyo, Japan

[73] Assignee: Japan Tobacco Inc., Tokyo, Japan

[21] Appl. No.: 284,214

[22] Filed: Aug. 2, 1994

[30] Foreign Application Priority Data

Aug. 2, 1993 [JP] Japan .................. 5-191066

[51] Int. Cl.⁶ .................................. A24C 5/60
[52] U.S. Cl. .......................... 131/280; 131/904
[58] Field of Search .................. 131/280, 281, 131/904, 908; 73/38

[56] References Cited

U.S. PATENT DOCUMENTS

| | | | |
|---|---|---|---|
| 4,154,090 | 5/1979 | Heitmann et al. | 73/38 |
| 4,177,670 | 12/1979 | Heitmann et al. | 73/38 |
| 4,223,551 | 9/1980 | Greve et al. | 73/38 |
| 4,912,964 | 4/1990 | Ohtsuki et al. | 73/38 |
| 4,955,398 | 9/1990 | Milner et al. | 131/904 X |
| 5,179,965 | 1/1993 | Komori et al. | 131/904 X |
| 5,186,183 | 2/1993 | Komori et al. | 131/904 X |

*Primary Examiner*—Jennifer Bahr
*Attorney, Agent, or Firm*—Birch, Stewart, Kolasch & Birch

[57] ABSTRACT

A dilution monitoring system for filter cigarettes has pairs of pressure sensors provided individually for left- and right-hand manufactured filter cigarettes, a dilution processor card adapted to receive pressure signals from the pressure sensors through an A/D converter, and a server computer connected to the processor card by means of a communication line and including a CRT. The dilution processor card computes the respective dilutions of the individual filter cigarettes in accordance with the pressure signals, and stores the computation results in a RAM. Thereafter, the processor card obtains quality data, such as the average, frequency distribution, and standard deviation of the stored dilutions, for each group of the left- and right-hand filter cigarettes, also stores the quality data in the RAM. The server computer receives the quality data transmitted from the processor card, and displays them in the form of a graph or table on the CRT.

10 Claims, 10 Drawing Sheets

DILUTION MONITORING SYSTEM FOR FILTER CIGARETTES

BACKGROUND OF THE INVENTION

1. Field of the Invention

The present invention relates to a system for monitoring dilutions of manufactured filter cigarettes.

2. Description of the Related Art

In a machine for manufacturing filter cigarettes or a so-called filter attachment, filter cigarettes are manufactured by connecting filters to cigarettes which are fed from a cigarette manufacturing machine. More specifically, the filter attachment is provided with a cigarette transportation path along which the cigarettes are transport in pairs. Each pair of cigarettes are arranged in a line on the transportation path, and are transported in a direction perpendicular to the axis thereof. After a filter plug is supplied between each pair of cigarettes, in the process of transporting the cigarettes, a paper piece is wound around the cigarettes and the filter plug. Thereupon, the cigarettes and the filter plug are connected to one another, thus forming a double filter cigarette. Thereafter, the double filter cigarette is cut in the center to be divided into two filter cigarettes, which are then separated axially from each other.

Further, the filter attachment comprises a device for detecting the respective dilutions of the manufactured filter cigarettes and a device for eliminating defective filter cigarettes, if any, in accordance with the results of detection by the detecting device. Thus, only nondefective filter cigarettes can be delivered from the filter attachment to a wrapping machine.

The detecting device can display the detected dilutions of the filter cigarettes on an analog or digital display device, which is located, for example, on a console panel of the filter attachment.

However, an operator of the filter attachment cannot easily grasp the trend of change of the dilutions of the filter cigarettes by the information from the display device only. In practice, therefore, the operator seizes the dilutions of the filter cigarettes indirectly by the incidence of defectives eliminated by means of the elimination device.

If the defectives increase, the operator must regulate the state of winding of the paper piece, which has a great influence on the dilutions of the filter cigarettes, or adjust the diameter of each cigarette rod manufactured by means of the cigarette manufacturing machine. By this time, however, numerous defectives will have already been produced.

Moreover, the detecting device can detect the dilution of only one of left- and right-hand filter cigarettes obtained by cutting each double filter cigarette, and cannot detect that of the other.

SUMMARY OF THE INVENTION

The object of the present invention is to provide a dilution monitoring system capable of accurately grasping the dilutions of all manufactured filter cigarettes on real-time basis and effectively controlling the dilutions.

The above object is achieved by a dilution monitoring system according to the present invention, which comprises: measuring means for measuring the respective dilutions of left- and right-hand manufactured filter cigarettes and outputting measurement results; collecting means for collecting the measurement results from the measuring means, the collecting means including a memory device for storing a predetermined number of up-to-date measurement results for each group of left- and right-hand filter cigarettes; processing means for obtaining quality data for each group of left- and right-hand filter cigarettes in accordance with the measurement results stored in the memory device of the collecting means; and receiving means for receiving the quality informations transmitted from the processing means, the receiving means including a display device for displaying the received quality informations in the form of a graph or table.

According to the monitoring system described above, the respective dilutions of the left- and right-hand manufactured filter cigarettes are measured individually, so that defective filter cigarettes, if any, can be securely eliminated in accordance with the results of the measurement.

Since the memory device of the collecting means is always stored with the up-to-date dilutions of the manufactured filter cigarettes, the computing means can obtain the quality informations, such as the average, frequency distribution, and standard deviation of the dilutions, in accordance with the up-to-date dilutions.

When the quality informations from the processing means are displayed in the form of a graph or table on the display device of the receiving means, therefore, an operator can easily grasp the state of current dilutions of the filter cigarettes, that is, the trend of change of the dilutions. Thus, in case of abnormal dilutions of the filter cigarettes, the operator can recognize the situation at once and quickly cope with this.

The measuring means may, for example, include a pair of first pressure sensors for individually detecting input pressures supplied to one end of the left- and right-hand filter cigarettes, a pair of second pressure sensors for individually detecting output pressures developing at the other ends of the filter cigarettes, and computing means for computing the respective dilutions of the left- and right-hand filter cigarettes in accordance with a differential pressure between pressure signals delivered from the first and second pressure sensors.

Preferably, in this case, the computing means includes detecting means for detecting the speed of manufacture of the left- and right-hand filter cigarettes and first correcting means for correcting the measurement results in accordance with the manufacturing speed detected by the detecting means. Also, the computing means may further include second correcting means for correcting the measurement results in accordance with the brand of the cigarettes to be manufactured. In the dilutions computed by the computing means are corrected by the first and second correcting means, the dilutions of the filter cigarettes can be measured more accurately.

The collecting means includes, for example, discriminating means for determining whether or not the measured dilutions of the individual filter cigarettes have normal values and means for storing the memory device with only those dilutions which are concluded to have normal values by the discriminating means. In this case, the discriminating means includes a sensor for determining whether or not the individual filter cigarettes are connected pneumatically between the first and second sensors when the respective dilutions of the filter cigarettes are to be measured.

The collecting means never stores the memory device with the measurement results from the measuring means when there are no filter cigarettes as objects of measurement, so that measurement data stored in the memory device accurately represent the dilutions of the manufactured filter cigarettes.

If the processing means is provided with a second memory device for storing the obtained quality data, it can continually prepare beforehand quality informations to be transmitted to the receiving means. When the receiving means gives a transmission command for the quality informations to the processing means, therefore, the processing means can immediately transmits the quality data to the receiving means.

BRIEF DESCRIPTION OF THE DRAWINGS

The present invention will become more fully understood from the detailed description given herein below and the accompanying drawings which are given by way of illustration only, and thus, are not limitative of the present invention, and wherein.

DETAILED DESCRIPTION OF THE PREFERRED EMBODIMENTS

Figure 1:
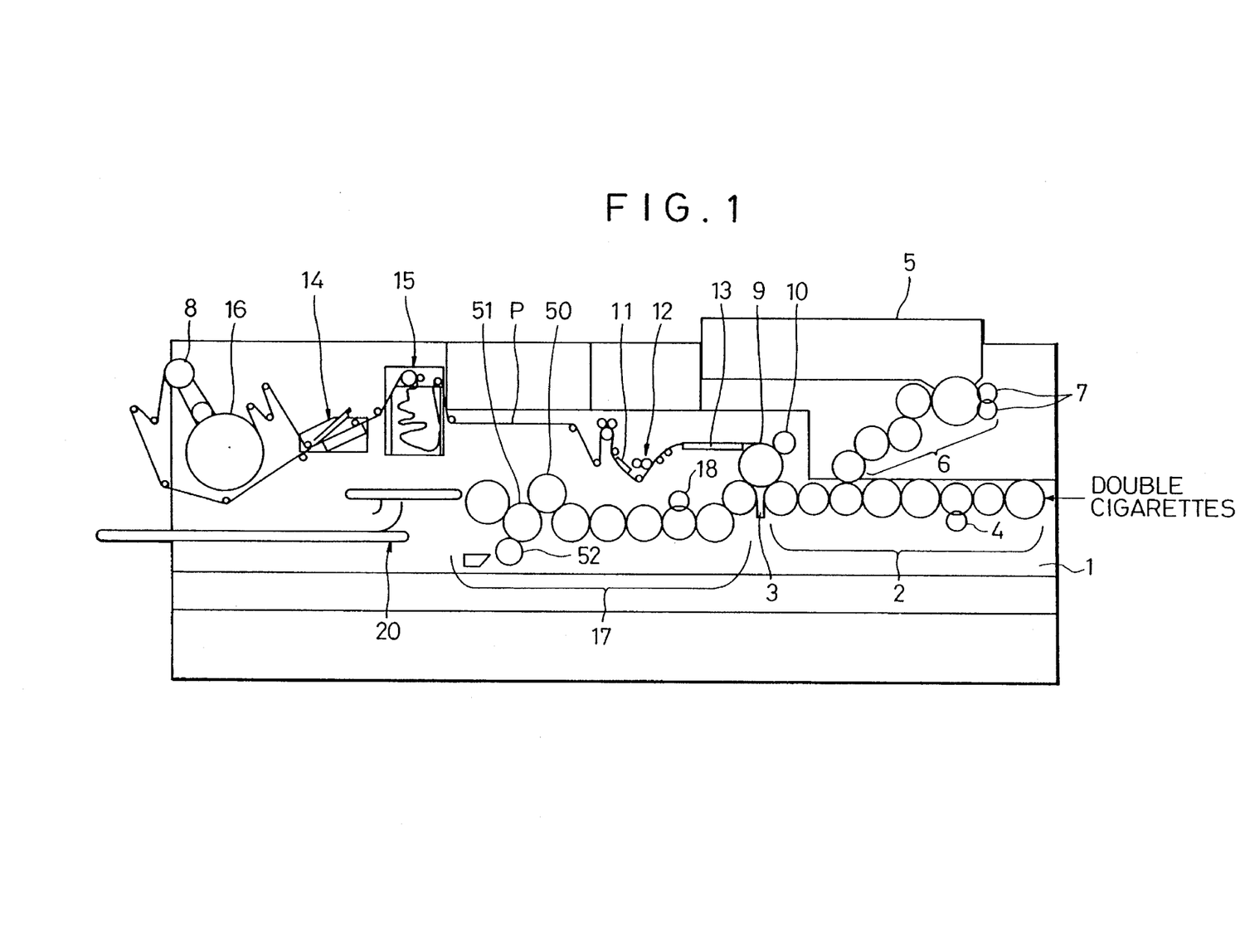
FIG. 1 is a schematic view showing a filter attachment.

Referring to FIG. 1, there is shown a filter attachment, which comprises an upright frame 1. The frame 1 is fitted with a drum train 2, which extends to the left from the right-hand end of the frame 1. The left-hand end of the drum train 2 is connected to a rolling section 3.

The drum train 2 includes a number of grooved drums, which are successively arranged adjacent to one another. The grooved drum which is situated at the right-hand end of the drum train 2 serves as a catcher drum, which can receive double cigarettes manufactured in a cigarette manufacturing machine (not shown). The double cigarettes received by the catcher drum are delivered to the rolling section 3 in a manner such that they transfer from one grooved drum to another adjacent thereto.

One of the grooved drums in the drum train 2 is provided with a rotary knife 4, which serves to cut each double cigarette on this drum into two equal parts or a pair of cigarettes. Thereafter, these two cigarettes are separated in their axial direction from each other.

Figure 2:
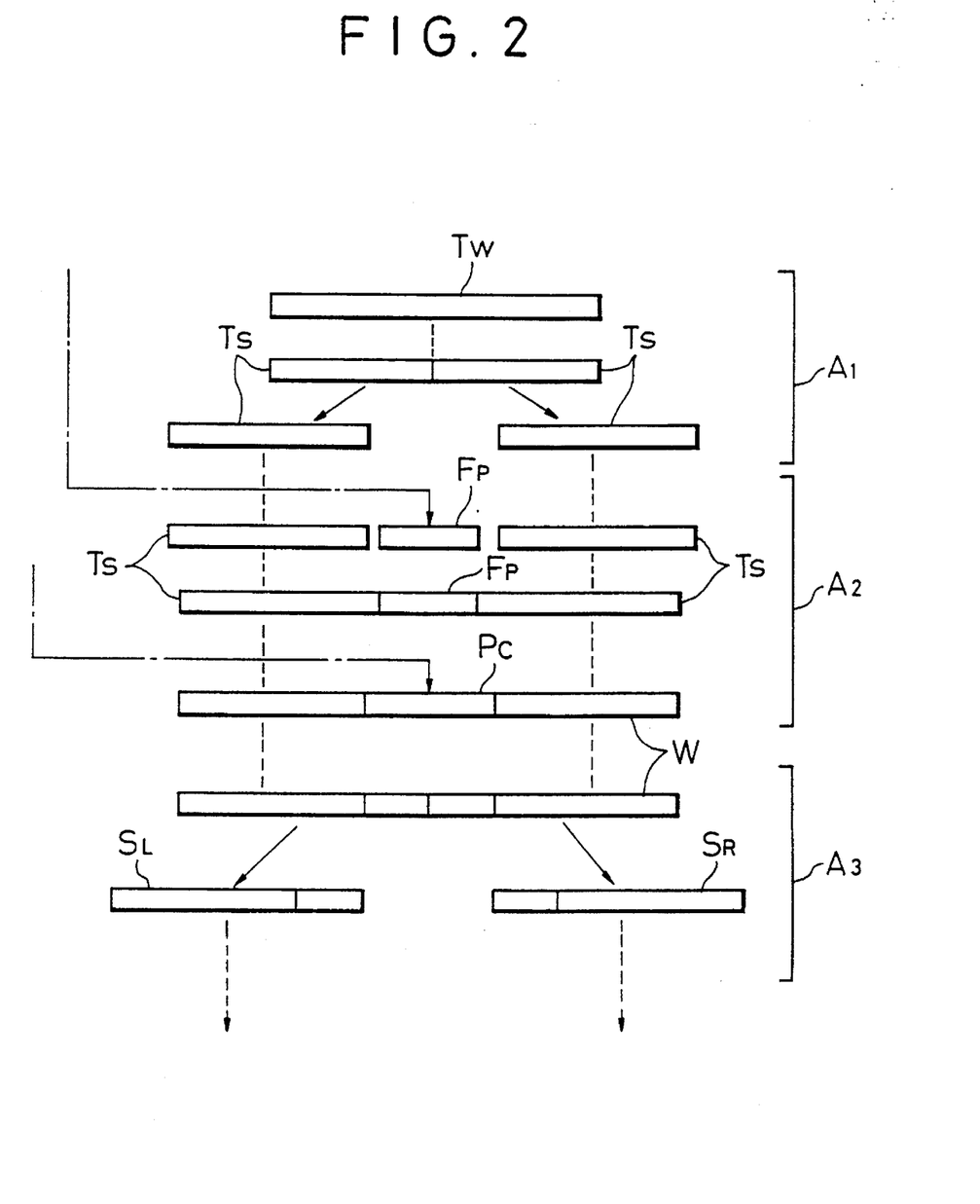
FIG. 2 is a diagram showing the procedure for connecting filter plugs with cigarettes.

In FIG. 2, symbol $A_1$ represents a region in which each double cigarette is processed, while $T_W$ and $T_S$ designate each double cigarette and each cigarette, respectively.

A hopper 5, which is located over the drum train 2, is stored with a number of filter rods. The hopper 5 and the drum train 2 are connected to each other by means of a drum train 6. The drum train 6, like the drum train 2, includes a number of grooved drums. The drum train 6 serves to pick up the filter rods one after another from the hopper 5 and transport them toward the drum train 2. In this process of transportation, each filter rod is divided into a plurality of equal parts, individual filter plugs, by means of rotary knives 7. Thereafter, these filter plugs are arranged in a line in the direction of transportation thereof. Thus, the drum train 6 supplies one filter plug between each pair of cigarettes on the drum train 2. Thereafter, the pair of cigarettes are individually brought into contact with the opposite ends of the filter plug, thus forming a double filter cigarette as a semi-finished product. This semi-finished product is delivered to the rolling section 3.

On receiving the semi-finished product, the rolling section 3 receives a paper piece having a paste-coated surface, and the paper piece is pasted on the center of the semi-finished product. When the semi-finished product is rotated about its axis on the rolling section 3, it is wound with the paper piece so that the two cigarettes and the filter plug are connected to one another, whereupon a double cigarette is obtained.

In FIG. 2, symbol $A_2$ represents a region in which each filter plug is supplied and wound with the paper piece, while $F_P$, $P_C$ and W designate the filter plug, paper piece, and double filter cigarette, respectively.

The paper piece is delivered from a receiving drum 9 to the rolling section 3. A paper web P, which is supplied from a paper roll 8 at the left-hand end portion of the frame 1, is guided to the drum 9. On the receiving drum 9, the web P is cut into individual paper pieces by means of an edged drum 10. Before the paper web P reaches the receiving drum 9, paste is applied to one side of the web P by means of a paste coater 12.

In FIG. 1, numerals 11, 13, 14, 15 and 16 denote a preheater, post-heater, web connector, reservoir, and spare paper roll, respectively, arranged in a paper web feed path which extends from the bobbin 8 to the receiving drum 9.

A drum train 17, which resembles the drum train 2, extends to the left from the rolling section 3. The drum train 17 serves to receive the double filter cigarette W from the rolling section 3 and transport it. In this process of transportation, the double filter cigarette is cut in the center by means of a rotary knife 18, whereupon two filter cigarettes are obtained. Thereafter, these two filter cigarettes, left and right, are separated in their axial direction from each other so that a predetermined space is secured between the filter cigarettes. In FIG. 2, symbol $A_3$ represents a region for this process, while $S_L$ and $S_R$ designate the individual filter cigarettes, separated left and right, respectively.

The drum train 17 is connected to a conveyor 20, and the manufactured filter cigarettes $S_L$ and $S_R$ are fed to a wrapping machine (not shown) by means of the conveyor 20.

Figure 3:
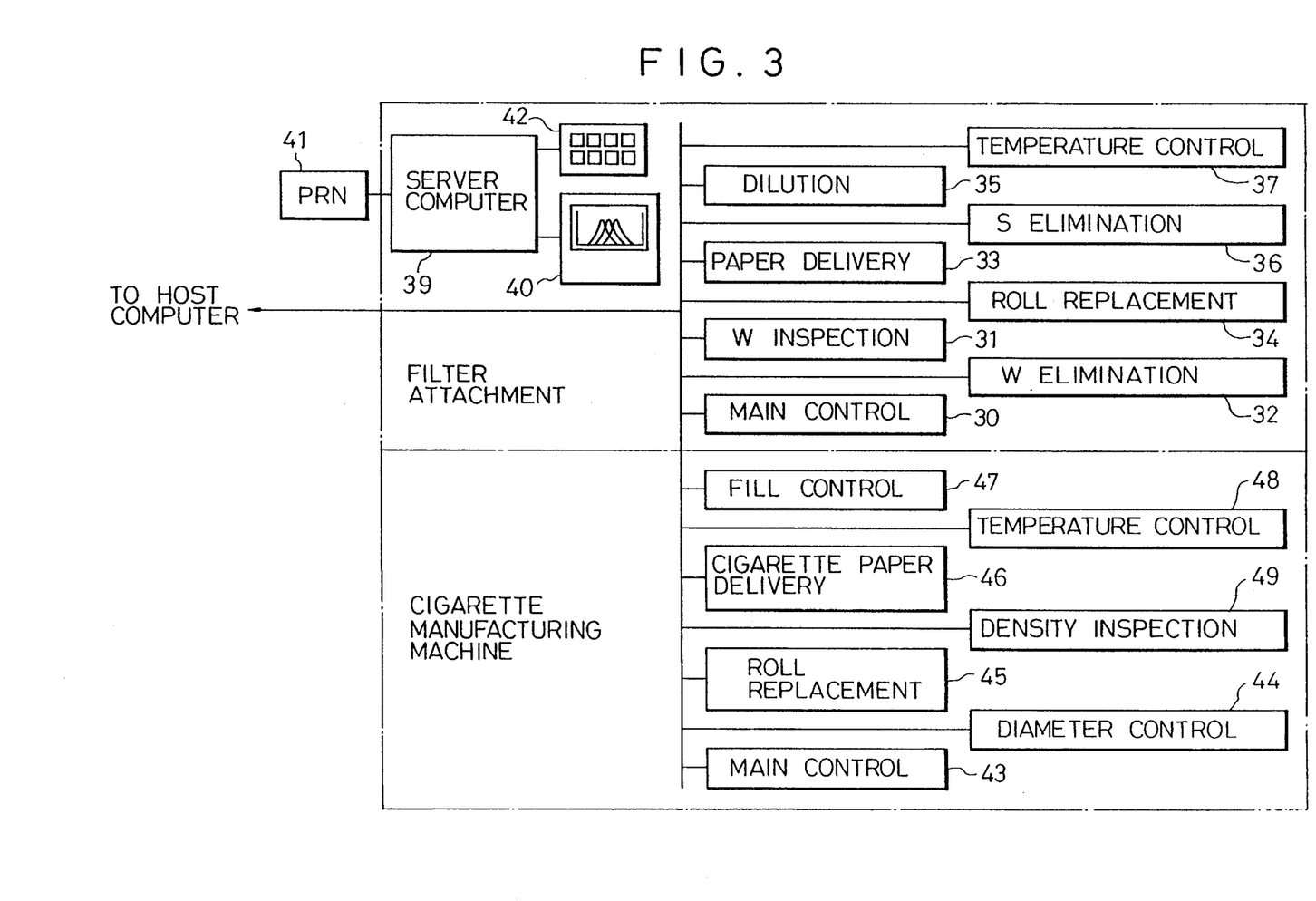
FIG. 3 is a block diagram showing examples of various control devices and inspection devices in the filter attachment.

The filter attachment is provided with various control devices and inspection devices for its operation. FIG. 3 shows examples of these devices.

These control and inspection devices include, for example, a main control device 30 for controlling the operation of the drum trains, a device 31 for inspecting the state of the paper pieces wound on the double filter cigarettes, a device 32 for removing the double filter cigarettes from the drum train 17 in accordance with the result of inspection by the inspection device 31, and a device 33 for controlling the delivery of the paper web. The devices further include a device 34 for controlling the replacement of the paper roll, a device 35 for detecting the dilutions of the filter cigarettes, a device 36 for removing the filter cigarettes from the drum train 17 in accordance with the result of inspection by the inspection device 35, and a device 37 for controlling the temperatures of the heaters.

These devices are connected to a server computer 39 by means of a communication line 38, and transmit informations on their control or inspection to the computer 39, automatically or in response to request commands from the computer 39.

The server computer 39, which is a so-called workstation, is connected with a CRT 40, a printer 41, a touch panel 42, etc. Also, the computer 39 is connected to a host computer by means of the communication line 38.

FIG. 3 shows examples of various control devices and inspection devices for the cigarette manufacturing machine. These devices include a main control device 43, a device 44 for controlling the diameter of the double cigarettes $T_W$ to be manufactured, a device 45 for controlling the replacement of the web roll of the cigarette paper, and a device 46 for controlling the delivery of the cigarette paper. The devices further include a device 47 for controlling the fill of cut tobacco in the cigarette rod to be manufactured, a device 48 for controlling the temperatures of the heaters of the cigarette manufacturing machine, and a device 49 for measuring the fill distribution of the cut tobacco in the cigarette rod.

The inspection device 35 of the filter attachment includes one grooved drum or inspection drum 50 in the drum train 17. The elimination device 36, which serves to eliminate defective filter cigarettes, if any, in cooperation with the inspection device 35, includes a grooved drum or elimination drum 51 which adjoins the inspection drum 50.

If a defective filter cigarette S is detected on the inspection drum 50, it transfers from the drum 50 to the elimination drum 51. Then, the defective filter cigarette 5 is removed from the drum 51. Thus, the defective filter cigarette cannot be transported toward the conveyor 20. In order to remove the defective filter cigarette 5 from the elimination drum 51, each groove of the elimination drum has a jet for compressed air. When compressed air is ejected from the jet, the defective filter cigarette in the groove is removed from the elimination drum 51, and falls onto a belt conveyor (not shown). This conveyor transports the defective filter cigarette to a recovery container (not shown).

The elimination drum 51 can separately receive the left- and right-hand filter cigarettes $S_L$ and $S_R$ on the drum train or the inspection drum 50. In FIG. 1, numeral 52 denote a sampling drum for sampling the left- and right-hand filter cigarettes from the drum 51.

As mentioned before, the inspection device 35 can detect the dilution of each of the filter cigarettes $S_L$ and $S_R$, and this dilution D may be defined as follows:

$$D=[(P_1-P_2)/P_1]\times 100,$$

where $P_1$ and $P_2$ represent an input pressure applied to the filter cigarette and an output pressure from the filter cigarette, respectively.

Figure 4:
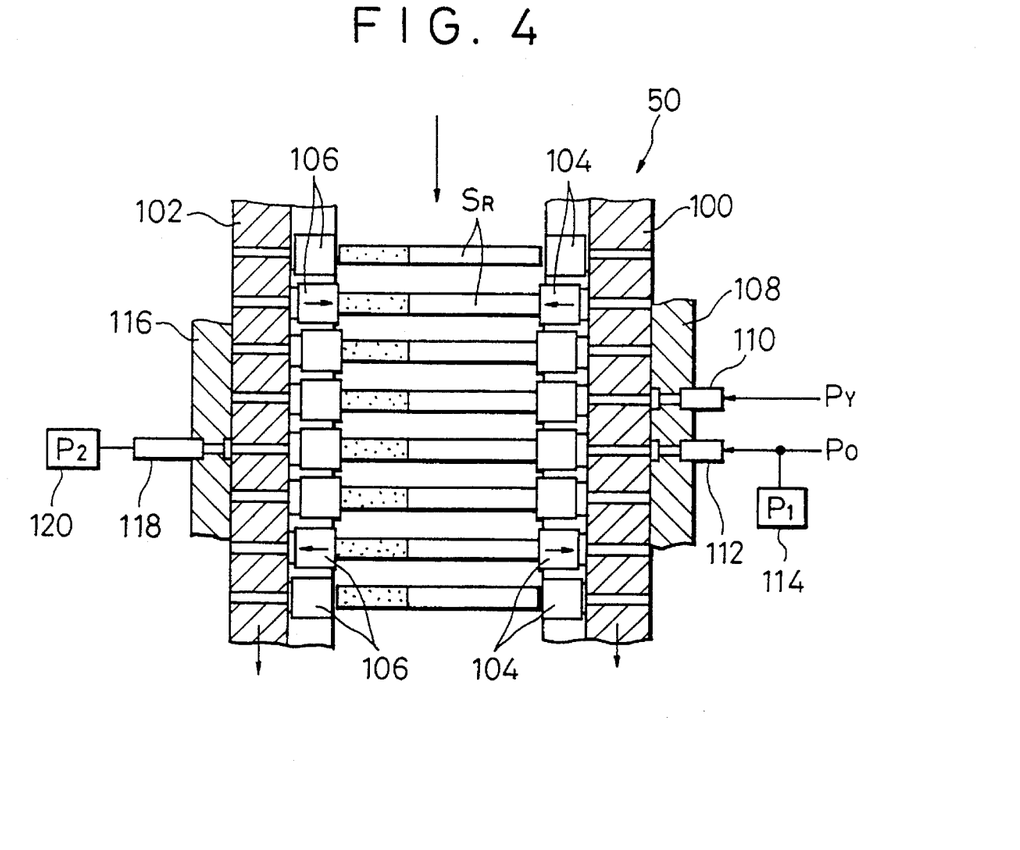
FIG. 4 is a view showing an inspection device for the dilutions of filter cigarettes.

FIG. 4 shows part of the peripheral surface of the inspection drum 50, that is, part of a peripheral surface used for the transportation of the filter cigarette $S_R$. The drum 50 has a number of grooves (not shown) on its peripheral surface. Each groove of the drum 50 can receive the filter cigarette $S_R$ from the grooved drum adjacent to the drum 50. The filter cigarette $S_R$ in the groove is transported as the inspection drum 50 rotates.

A pair of rings 100 and 102 are arranged on either side of the grooves on the outer peripheral surface of the inspection drum 50. The rings 100 and 102 rotate in one with the drum 50. The rings 100 and 102 have their respective suction pads 104 and 106 situated corresponding to the opposite ends of the grooves. When the corresponding grooves pass a predetermined rotational angle region as the inspection drum 50 rotates, the suction pads 104 and 106 are pushed out toward the filter cigarettes $S_R$ in the grooves by the action of a cam mechanism (not shown). Thus, each filter cigarette $S_R$ transported on the drum 50 is held between its corresponding pair of pads 104 and 106.

A control ring 108 is nonrotatably mounted outside the one ring 100 so that the ring 100 can rotate in sliding contact with the ring 108. A pilot pressure pipe 110 and an input pressure pipe 112 are connected separately to the control ring 108. The pilot pressure pipe 110 is connected to a subpneumatic source, which feeds a pilot pressure $P_Y$ into the pipe 110. The input pressure pipe 112 is connected to a main pneumatic source, which supplies a main pressure $P_O$ ($P_Y$) to the pipe 112. Moreover, the input pressure pipe 112 is connected with a pressure sensor 114 which, formed of a semiconductor pressure transducer, detects the input pressure in the pipe 112.

Also, a control ring 116 is nonrotatably mounted outside the other ring 102 so that the ring 102 can rotate in sliding contact with the ring 116. An output pressure pipe 118 is connected to the control ring 116, and is located at the same angular position with the input pressure pipe 112. The output pressure pipe 118 is connected with a pressure sensor 120 which, formed of a semiconductor pressure transducer, detects the pressure in the pipe 118.

As the filter cigarette $S_R$ on the inspection drum 50 is transported with the drum 50 in rotation, it is held between its corresponding pair of suction pads 104 and 106. When the rotation of the inspection drum 50 advances so that the one suction pad 104 is connected to the pilot pressure pipe 110 by means of the internal passage of the ring 100, the pilot pressure $P_Y$ is applied to the filter cigarette $S_R$ through the pipe 110 and the pad 104.

When the rotation of the inspection drum 50 further advances, thereafter, the suction pad 104 is connected to the input pressure pipe 112 by means of the internal passage of the ring 100, and the filter cigarette $S_R$ is subjected to the main pressure $P_O$ from the input pressure pipe 112. At this time, the other suction pad 106 is connected to the output pressure pipe 118 by means of the internal passage of the ring 102.

At this point in time, the pressure sensor 114 detects input pressure $P_1$ applied to the filter cigarette $S_R$, while the pressure sensor 120 detects the output pressure $P_2$ from the cigarette $S_R$. Thereupon, the inspection device 35 computes the dilution D of the filter cigarette $S_R$ on the basis of these pressures $P_1$ and $P_2$ and according to the aforementioned equation.

Figure 5:
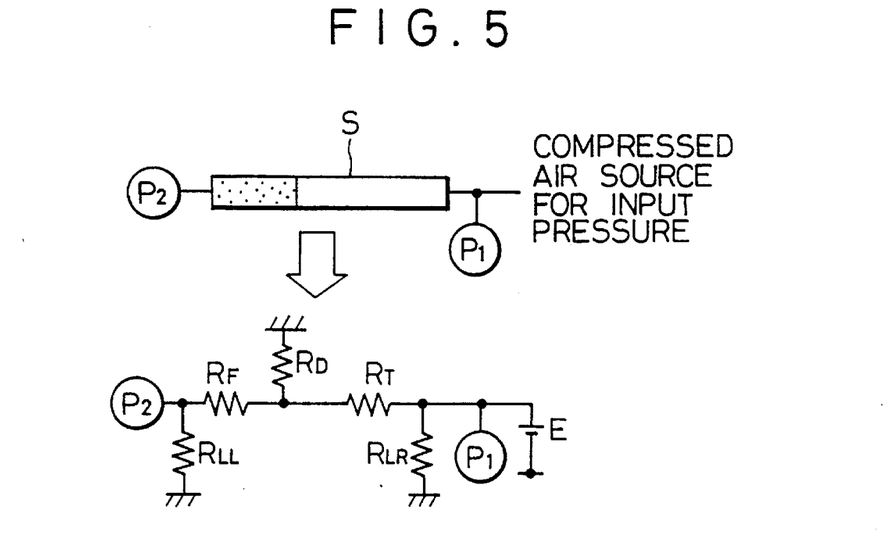
FIG. 5 is an equivalent circuit diagram for illustrating the principle of measurement of the dilutions.

The principle of dilution measurement using the pressure sensors 114 and 120 can be represented by an equivalent circuit shown in FIG. 5. In this equivalent circuit diagram, symbol E represents a voltage equivalent to the main pressure $P_O$; $R_T$, equivalent resistance of each cigarette; $R_F$, equivalent resistance of each filter; and $R_{LR}$ and $R_{LL}$, equivalent resistances corresponding to the leakage pressures from the left- and right-hand suction pads 104 and 106, respectively. Moreover, symbol $R_D$ represents an equivalent resistance of air which passes through a number of apertures, if any, in the filter portion of each filter cigarette $S_R$. The apertures in the filter portion are previously formed in the paper web, for example.

As mentioned above, detection of the dilution of each filter cigarette S requires use of the pair of pressure sensors 114 and 120. When the pairs of filter cigarettes $S_L$ and $S_R$, left and right, are transported synchronously on the inspection drum 50, therefore, detection of the respective dilutions of these filter cigarettes $S_L$ and $S_R$ require use of two pairs of pressure sensors 114 and 120, as shown in FIG. 6.

Figure 6:
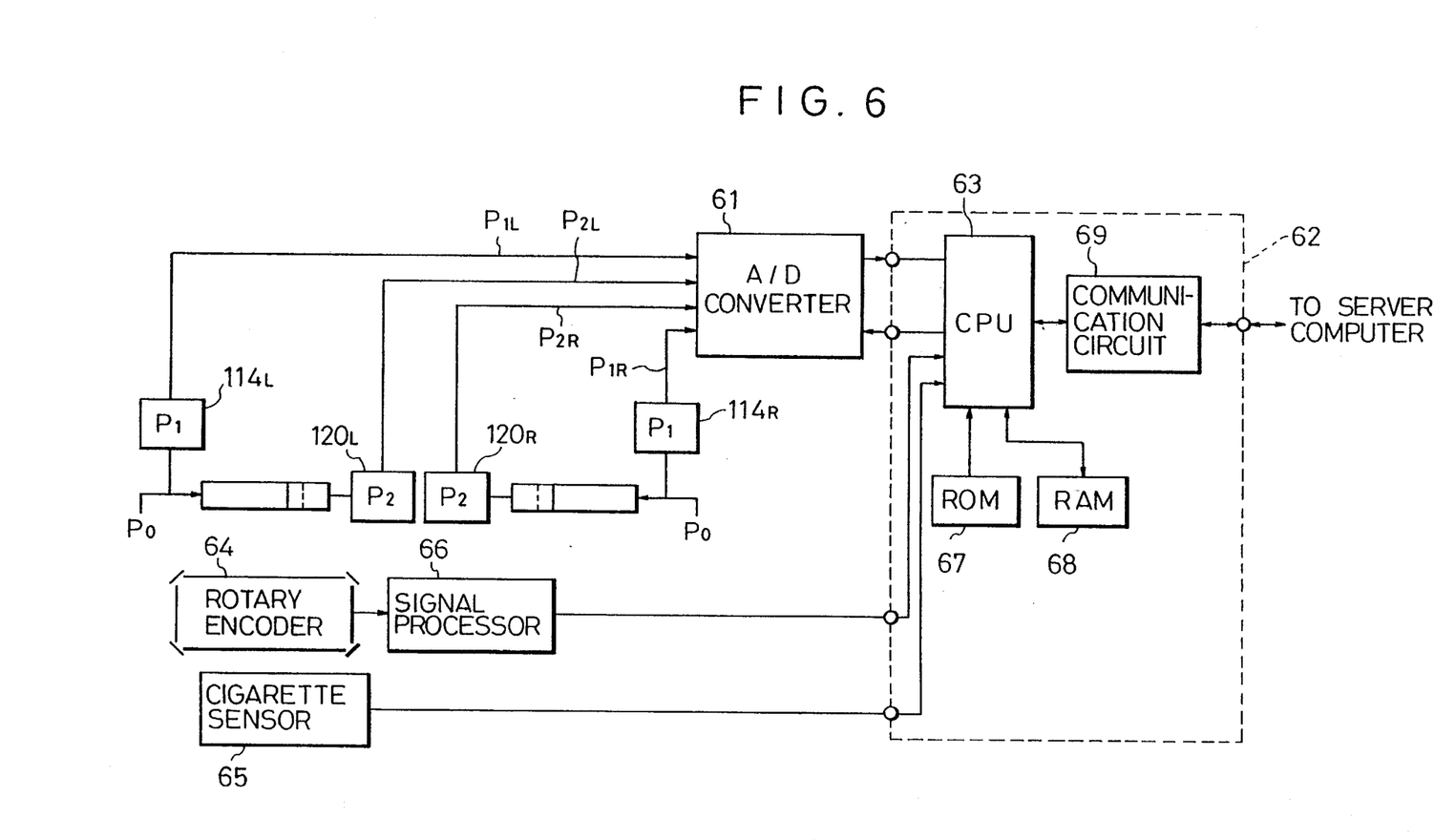
FIG. 6 is a block diagram showing part of a dilution monitoring system according to one embodiment of the present invention.

In FIG. 6, pressure sensors $114_L$ and $120_L$ are used to examine the dilutions of the filter cigarettes $S_L$ which are transported on the left-hand side of the peripheral surface of the inspection drum 50. Another pair of pressure sensors $114_R$ and $120_R$ are used to examine the dilutions of the filter cigarettes $S_R$ which are transported on the right-hand side of the peripheral surface of the drum 50.

Analog pressure signals are delivered from the pressure sensors 114 and 120, and are supplied to an A/D converter 61. The converter 61 removes noises from the pressure signals or input signals, then converts these signals into digital signals, and outputs the digital signals. Thus, the digital pressure signals are supplied from the A/D converter 61 to a CPU 63 of a dilution processor card 62.

On the other hand, the inspection device 35 includes a rotary encoder 64 and a pair of cigarette sensors 65, besides the pressure sensors. The rotary encoder 64 detects the operating speed of the filter attachment, and delivers its detection signal to a signal processor circuit 66. Based on this detection signal, the processor circuit 66 outputs synchronizing signals, which are supplied to the CPU 63 of the processor card 62. The synchronizing signals are pulse signals which are used to cause the pressure signals delivered from the pressure sensors 114 and 120 to correspond to the left- and right-hand filter cigarettes $S_L$ and $S_R$ as objects of detection on the inspection drum 50.

The cigarette sensors 65 detect the presence of the filter cigarettes $S_L$ and $S_R$ in the grooves of the inspection drum 50 when the dilutions of the filter cigarettes are detected, and supplies detection signals to the CPU 63.

The CPU 63 calculates the respective dilutions D of the individual filter cigarettes S in accordance with a program stored in a ROM 67, and stores the results of the calculation into a RAM 68. Moreover, the CPU 63 tabulates the calculation results on the dilutions D, and obtains various dilution informations in accordance with the result of the tabulation. These dilution informations are also stored into the RAM 68. Furthermore, the CPU 63 can transmit the dilution informations stored in the RAM 68 to the server computer 39 through a communication circuit 69 and the communication line 38.

Figure 7:
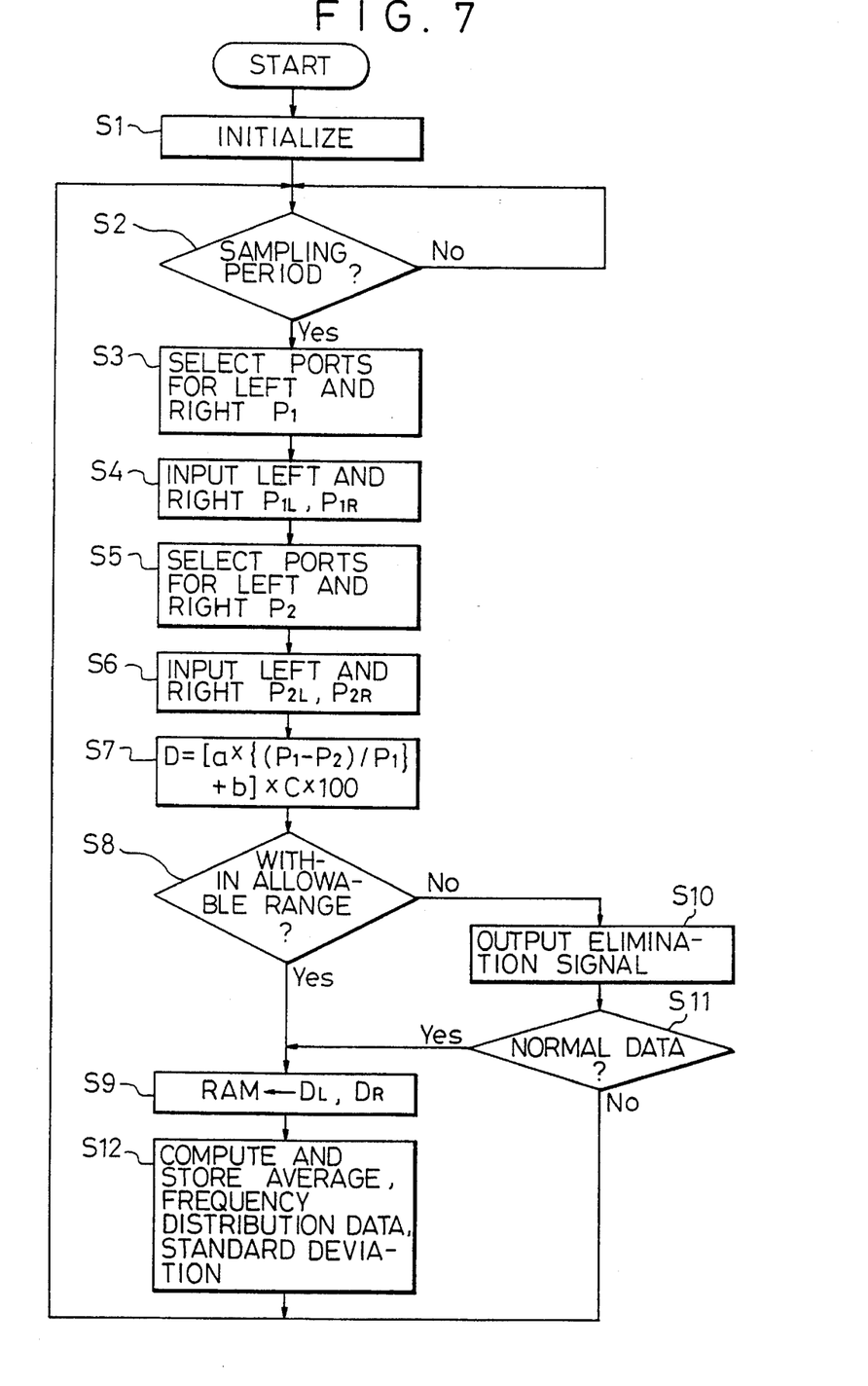
FIG. 7 is a flow chart showing a main routine executed by a CPU shown in FIG. 6.

Referring to FIG. 7, there is shown a main routine executed in the inspection device 35. The following is a description of this main routine.

Main Routine

First, the A/D converter 61 and the processor card 62 are initialized in the inspection device 35 (Step S1). Then, the CPU 63 of the processor card 62 determines whether or not the pressure signals from the pressure sensors, that is, the digital signals from the A/D converter 61, should be sampled (Step S2). More specifically, the CPU 63 determines whether or not the synchronizing signals from the signal processor circuit 66 are received. If the decision in this step is NO, the CPU 63 repeats the execution of the process of Step S2. When the decision in Step S2 becomes YES, the CPU 63 selects a pair of first input ports (not shown) of the A/D converter 61 to which the pressure sensors $114_L$ and $114_R$ are connected individually (Step S3). Thereupon, the first input ports of the converter 61 are opened, and pressure signals $P_{1L}$ and $P_{1R}$ from the pressure sensors $114_L$ and $114_R$ are applied the converter 61 through the first input ports, individually (Step S4). These pressure signals $P_{1L}$ and $P_{1R}$ are supplied to the CPU 63 after they are converted into digital signals in the A/D converter 61.

Then, the CPU 63 selects a pair of second input ports (not shown) of the A/D converter 61 to which the pressure sensors $120_L$ and $120_R$ are connected individually (Step S5). Thereupon, the second input ports of the converter 61 are opened, and pressure signals $P_{2L}$ and $P_{2R}$ from the pressure sensors $120_L$ and $120_R$ are applied the converter 61 through the second input ports, individually (Step S6). These pressure signals $P_{2L}$ and $P_{2R}$ are also supplied to the CPU 63 after they are converted into digital signals in the A/D converter 61.

Based on the received pressure signals $P_1$ and $P_2$ for the individual filter cigarettes $S_L$ and $S_R$, the CPU 63 computes the respective dilutions D of the filter cigarettes (Step S7). The dilutions D are computed according to the following equation.

$$D\ (\%) = |a \times \{(P_1 - P_2)/P_1\} + b| \times c \times 100.$$

In this equation, a and b represent correction factors for the variation of the brands of the filter cigarettes and changes attributable to mechanical adjustment of the filter attachment and the like, respectively, while c represents a correction gain for the operating speed (peripheral speed of each drum of the drum trains) of the filter attachment.

The correction gain c is obtained from the result of a basic operation test on the filter attachment. The operation test indicates that the higher the operating speed of the filter attachment, the greater is the margin by which the detected value of the dilution exceeds the actual value. According to the aforesaid equation, therefore, the dilution D is obtained by multiplying a reference dilution DO (=a× $\{(P_1-P_2)/P_1\}$+ b) by the correction gain c.

The correction factors a and b are constants which are set before the start of operation of the filter attachment, while the correction factor c is a variable which varies depending on the operating speed of the filter attachment. In order to settle the correction gain c, therefore, the operating speed of the filter attachment must be detected. The operating speed can be detected in the CPU 63 by the number of synchronizing signals generated per unit time.

In the aforesaid equation for the computation of the dilutions D, the subscripts $_L$ and $_R$ corresponding to the left- and right-hand filter cigarettes are not affixed to $P_1$ and $P_2$ for the first and second pressure signals. Actually, however, the dilutions D are computed individually in accordance with the first and second pressure signals $P_1$ and $P_2$ with the same subscript.

When dilutions $D_L$ and $D_R$ of the left- and right-hand filter cigarettes $S_L$ and $S_R$ are computed individually in the aforesaid manner, the CPU 63 determines whether or not the computed dilutions $D_L$ and $D_R$ are within an allowable range (Step S8). The allowable range for the dilutions D varies depending on the brands of the filter cigarettes. The allowable range for filter cigarettes of some brands ranges from 45% to 55%.

If the decision in Step S8 is YES, the CPU 63 stores the computed dilutions $D_L$ and $D_R$ into the RAM 68 (Step S9).

If the decision in Step S8 is NO, on the other hand, the CPU 63 outputs an elimination signal (Step S10), and then determines whether or not the dilutions D are normal data (Step S11). More specifically, the decision in Step S11 is made in accordance with the detection signals from the cigarette sensor 65, for example.

Even though the dilutions D are not within the allowable range, the CPU 63 stores them as normal data in the RAM 68 only if the values of the dilutions D are the results of actual inspection of the filter cigarettes S (or if the presence of the filter cigarettes S is ascertained by the detection signals from the cigarette sensors 65). If the decision in Step S11 is NO, however, the CPU 63 repeatedly executes the processes of Step S2 and the subsequent steps without storing the dilutions D into the RAM 68.

The discrimination in Step S8 is carried out independently for each of the dilutions $D_L$ and $D_R$ of the left- and right-hand filter cigarettes, so that the elimination signal outputted in Step S10 specifies the left- or right-hand filter cigarette $S_L$ or $S_R$, whichever may be defective. On receiving the elimination signal, therefore, the elimination device 36 eliminates only that filter cigarette S which corresponds to the elimination signal from the drum train 17.

In Step S12, the CPU 63 tabulates data for the dilutions $D_L$ and $D_R$ stored in the RAM 68, computes data to be visualized, for the dilutions D of the left- and right-hand filter cigarettes or all the filter cigarettes as a whole, that is, the average, frequency distribution, standard deviation, etc. of the dilutions, and stores the results of computation as dilution data into the RAM 68.

Figure 8:
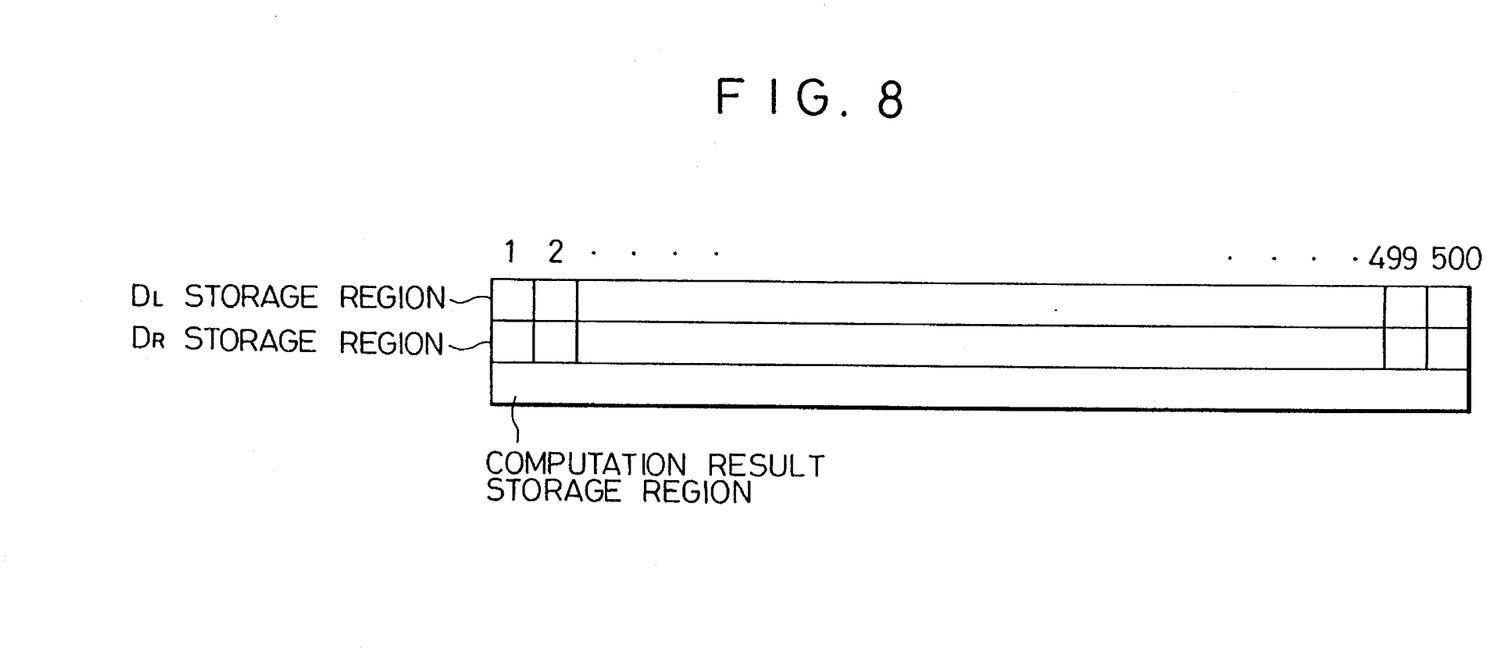
FIG. 8 is a diagram showing data storage regions in a RAM shown in FIG. 6.

Thereafter, the CPU 63 repeatedly executes the processes of Step S2 and the subsequent steps, whereupon the dilutions $D_L$ and $D_R$ of the pairs of filter cigarettes are stored successively into the RAM 68. As shown in FIG. 8, the RAM 68 can store data for the dilutions $D_L$ and $D_R$ of, e.g., 1,000 filter cigarettes S, 500 on each side. When the number of data for the data on the dilutions D exceeds 500, the CPU 63 restores up-to-date data in place of the oldest data in the RAM 68.

Thus, the data on the dilutions D are updated successively in accordance with the up-to-date data number for each 500 filter cigarettes.

Figure 9:
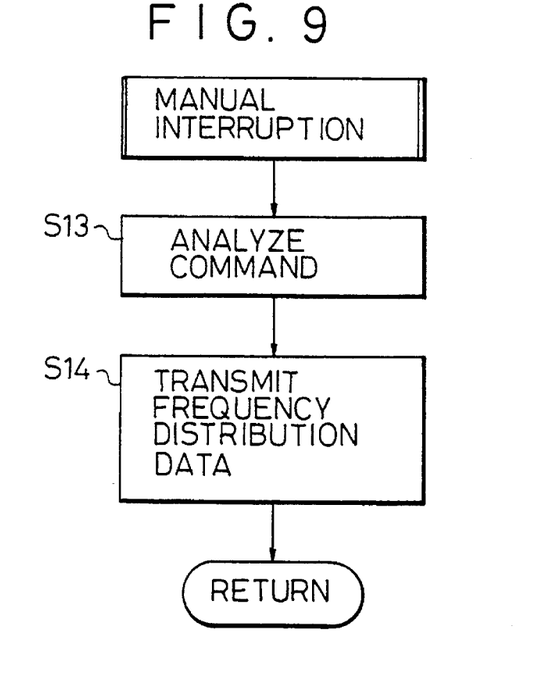
FIG. 9 is a flow chart showing a manual interruption routine executed by the CPU.

On receiving a manual interruption command from the server computer 39, the CPU 63 executes an interruption routine shown in FIG. 9.

Manual Interruption Routine

In this interruption routine, the CPU 63 analyzes the interruption command (Step S13). Based on the result of this analysis, the CPU 63 transmits up-to-date data on the dilutions D stored in the RAM 68, e.g., dilution frequency distribution data, to the server computer 39 through the communication circuit 69 and the communication line 38 (Step S14).

When an operator operates the touch panel 42, a manual interruption signal is supplied from the server computer 39 to the CPU 63.

Meanwhile, the server computer 39 can automatically supply an interruption command to the CPU 63 at predetermined time intervals, e.g., at intervals of 3 minutes. On receiving this interruption signal, the CPU 63 executes a timer interruption routine shown in FIG. 10.

Timer Interruption Routine

Figure 10:
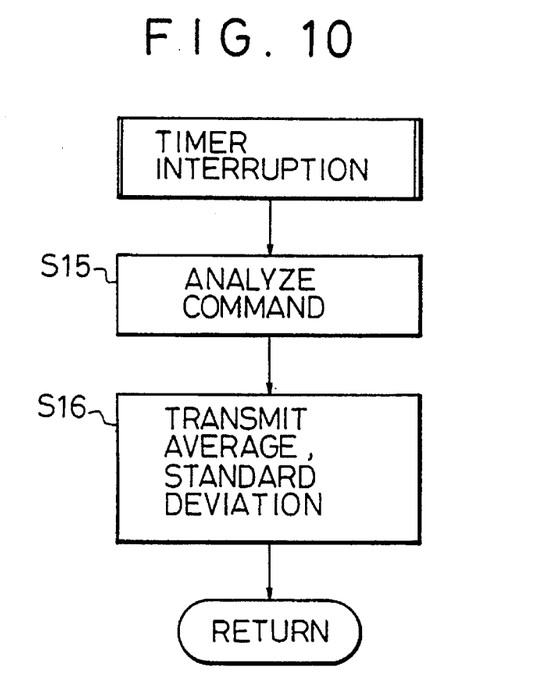
FIG. 10 is a flow chart showing a timer interruption routine executed by the CPU.

In this interruption routine, the CPU 63 analyzes the interruption command (Step S15). Based on the result of this analysis, the CPU 63 transmits up-to-date data on the dilutions D stored in the RAM 68, e.g., average and standard deviation of the dilutions D, to the server computer 39 through the communication circuit 69 and the communication line 38 (Step S16).

Figure 11:
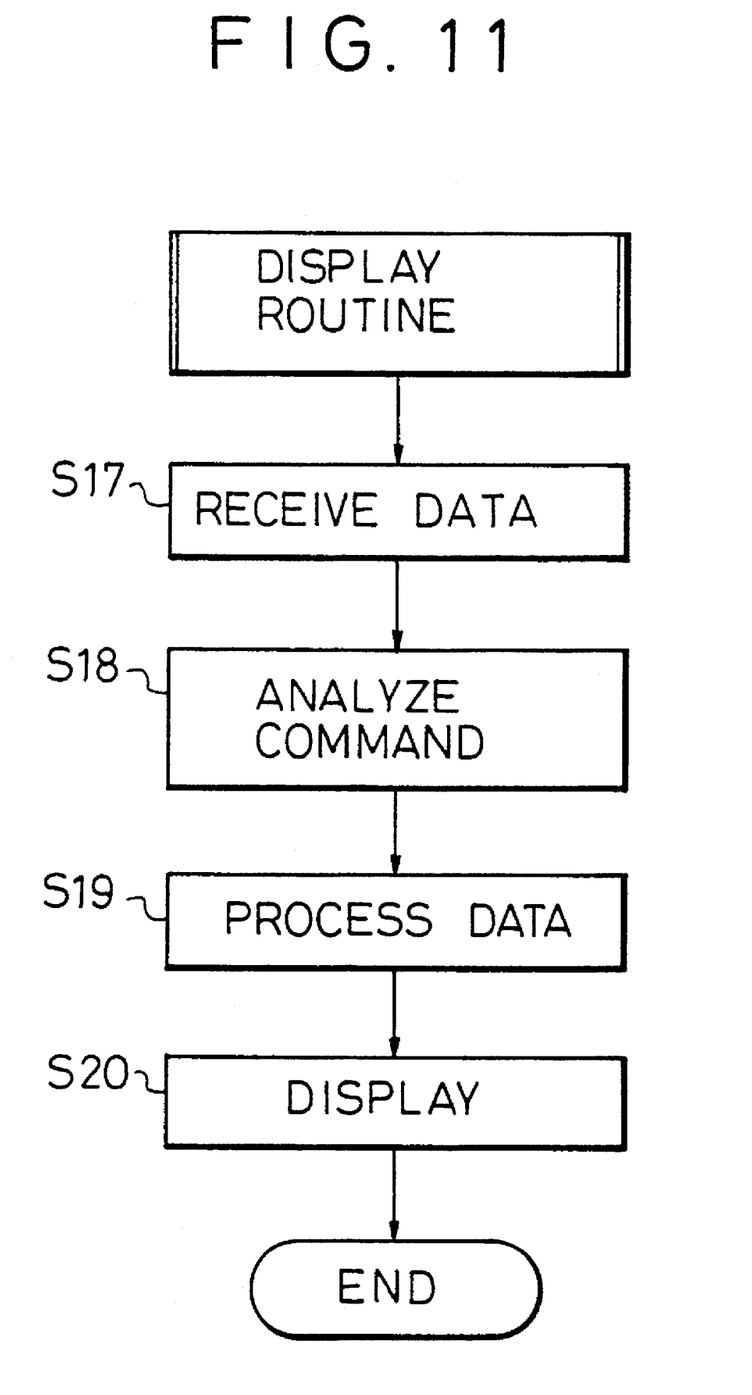
FIG. 11 is a flow chart showing a display routine executed by a server computer.

On the other hand, an interruption command is transmitted from the sever computer 39 to the CPU 63, the server computer 39 executes a display routine shown in FIG. 11.

Display Routine

In this display routine, the server computer 39 receives data transmitted from the dilution processor card 62 or the CPU 63 (Step S17), and analyzes the interruption command given to the CPU 63 (Step S18). Thereafter, the computer 39 executes data processing corresponding to the transmitted interruption command and the received data (Step S19), and displays the result of the processing on the CRT 40.

Figure 12:
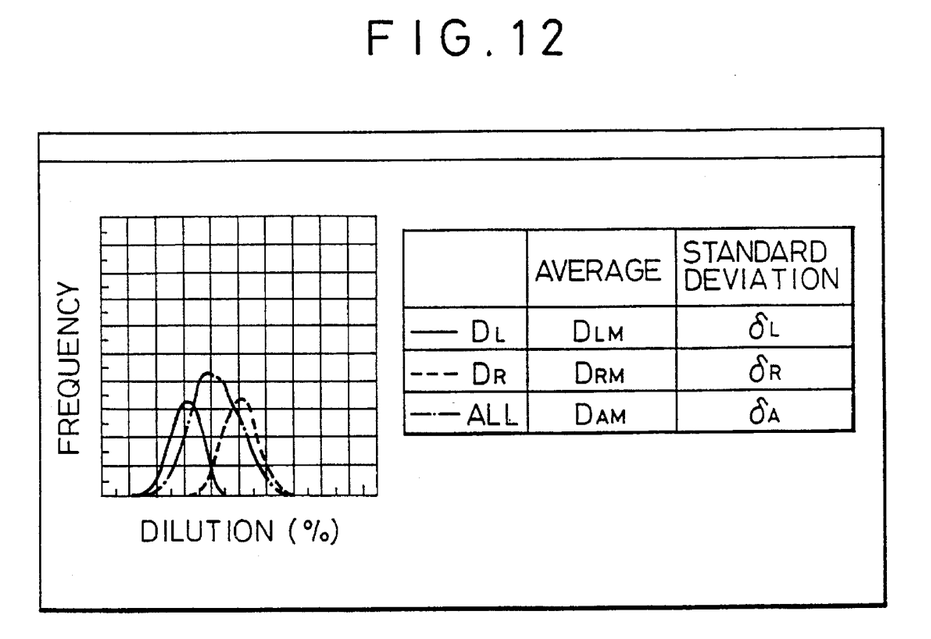
FIG. 12 is a diagram showing data displayed on a CRT by means of the server computer.

More specifically, when the interruption command is issued by the operator's manual operation, the server computer 39 receives the frequency distribution data for the dilutions D from the CPU 63. Thereupon, the computer 39 displays on the screen of the CRT 40 graphic patterns of frequency distributions for the dilutions $D_L$ (full line) and $D_R$ (broken line) of the left- and right-hand filter cigarettes and dilution $D_A$ (dashed line) of all the filter cigarettes as a whole, as shown in FIG. 12.

Thus, the operator can easily grasp the trend of change of the dilutions D of the filter cigarettes, manufactured by means of the filter attachment, according to the dilution frequency distributions displayed on the CRT 40.

Since the frequency distributions for the dilutions $D_L$ and $D_R$ of the left- and right-hand filter cigarettes are displayed simultaneously on the CRT 40, moreover, the operator can also independently grasp the trend of change of the dilutions of the left- and right-hand filter cigarettes with high accuracy.

The frequency distributions can be displayed on the CRT 40 by the operator's manual operation only, so that the operator can easily recognize the dilution frequency distribution at a desired time.

Figure 13:
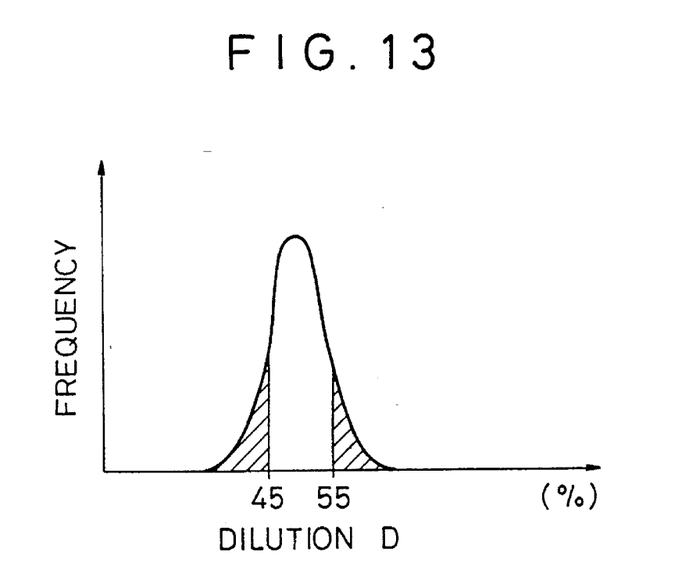
FIG. 13 is a diagram showing the dilution distribution of manufactured filter cigarettes.

In the main routine, furthermore, the process of Step S9 is executed following Step S11, so that the frequency distribution for the dilutions $D_L$ and $D_R$ displayed on the CRT 40 involves data for defectives hatched in FIG. 13. Accordingly, the operator can grasp the dilution state more accurately.

Thus, if the frequency distribution for the dilutions D of the filter cigarettes on one side is deviated one-sidedly from the allowable range, for example, the operator can immediately recognize this situation. In this case, the operator can stop the operation of the filter attachment at once and quickly adjust the attachment, so that the incidence of defective filter cigarettes can be lowered.

If an interruption command is generated by timer interruption from the server computer 39, on the other hand, the computer 39 displays the average and standard deviation of the dilutions $D_L$, $D_R$ and $D_A$ received from the CPU 63 in the form of a table on the screen of the CRT 40, as shown in FIG. 12.

Since this table is displayed periodically on the screen of the CRT 40, the operator can grasp the state of the dilutions D by the table without displaying any graphs for the dilution frequency distributions.

As mentioned before, the server computer 39 only receives data obtained by computation in the dilution processor card 62, and displays quality control data, such as the frequency distributions, on the CRT 40 in accordance with the computation data. Thus, the load on the computer 39 can be lightened.

The server computer 39 can cause the printer 41 to print frequency distribution graphs and the table, and also store data transmitted from the CPU 63. In this case, the computer 39 can obtain data on dilutions for one day or more, for example.

What is claimed is:

1. A system for monitoring dilutions of manufactured filter cigarettes, the manufactured filter cigarettes being transported in pairs and forming a pair of flows of left-hand and right-hand filter cigarettes, comprising:

measuring means for measuring the respective dilutions of the left-hand and right-hand filter cigarettes and outputting measurement results;

collecting means for collecting the measurement results from said measuring means, said collecting means including a memory device for storing a predetermined number of up-to-date measurement results for each flow of the left-hand and right-hand filter cigarettes;

first processing means for obtaining quality data on the dilutions for each flow of the left-hand and right-hand filter cigarettes in accordance with the measurement results stored in the memory device of said collecting means, said first processing means including transmitting means for transmitting the quality data obtained; and second processing means for obtaining graph or table on the dilutions of the manufactured filter cigarettes in accordance with the quality data, said second processing means including receiving means for receiving the quality data transmitted from the transmitting means by means of a two-way communication line, and a display device for displaying the graph or table.

2. The system according to claim 1, wherein said measuring means includes a pair of first pressure sensors for individually detecting input pressures supplied to one end of the left-hand and right-hand filter cigarettes, a pair of second pressure sensors for individually detecting output pressures developing at the other end of the filter cigarettes, and computing means for computing the respective dilutions of the left-hand and right-hand filter cigarettes in accordance with a differential pressure between pressure signals delivered from the first and second pressure sensors.

3. The system according to claim 2, wherein said collecting means includes discriminating means for determining whether or not the measured dilutions of the individual filter cigarettes have normal values and means for storing the memory device with only those dilutions which are concluded to have normal values by the discriminating means.

4. The system according to claim 3, wherein said discriminating means includes a sensor for determining whether or not the individual filter cigarettes are connected pneumatically between the first and second sensors when the respective dilutions of the filter cigarettes are to be measured.

5. A system for monitoring dilutions of manufactured filter cigarettes, the manufactured filter cigarettes being transported in pairs and forming a pair of flows of left-hand and right-hand filter cigarettes, comprising:

measuring means for measuring the respective dilutions of the left-hand and right hand filter cigarettes and outputting measurement results;

collecting means for collecting the measurement result from said measuring means, said collecting means including a memory device for storing a predetermined number of up-to-date measurement results for each flow of the left-hand and right-hand filter cigarettes;

first processing means for obtaining quality data on the dilutions for each flow of the left-hand and right-hand filter cigarettes in accordance with the measurement results stored in the memory device of said collecting means, said first processing means including transmitting means for transmitting the quality data obtained; and second processing means for obtaining a graph or table on the dilutions of the manufactured filter cigarettes in accordance with the quality data, said second processing means including receiving means for receiving the quality data transmitted from the transmitting means by means of a two-way communication line, and a display device for displaying the graph or table;

said measuring means includes a pair of first pressure sensors for individually detecting input pressures supplied to one end of the left-hand and right-hand filter cigarettes, a pair of second pressure sensors for individually detecting output pressures developing at the other end of the filter cigarettes, and computing means for computing the respective dilutions of the left-hand and right-hand filter cigarettes in accordance with a differential pressure between pressure signals delivered from the first and second pressure sensors, said computing means includes detecting means for detecting the speed of manufacture of the left-hand and right-hand filter cigarettes and first correcting means for correcting the measurement results in accordance with the manufacturing speed detected by the detecting means.

6. The system according to claim 5, wherein said collecting means includes discriminating means for determining whether or not the measured dilutions of the individual filter cigarettes have normal values and means for storing the memory device with only those dilutions which are concluded to have normal values by the discriminating means.

7. The system according to claim 6, wherein said discriminating means includes a sensor for determining whether or not the individual filter cigarettes are connected pneumatically between the first and second sensors when the respective dilutions of the filter cigarettes are to be measured.

8. A system for monitoring dilutions of manufactured filter cigarettes, the manufactured filter cigarettes being transported in pairs and forming a pair of flows of left-hand and right-hand filter cigarettes, comprising:

measuring means for measuring the respective dilutions of the left-hand and right hand filter cigarettes and outputting measurement results;

collecting means for collecting the measurement results from said measuring means, said collecting means including a memory device for storing a predetermined number of up-to-date measurement results for each flow of the left-hand and right-hand filter cigarettes;

first processing means for obtaining quality data on the dilutions for each flow of the left-hand and right-hand filter cigarettes in accordance with the measurement results stored in the memory device of said collecting means, said first processing means including transmitting means for transmitting the quality data obtained; and second processing means for obtaining a graph or table on the dilutions of the manufactured filter cigarettes in accordance with the quality data, said second processing means including receiving means for receiving the quality data transmitted from the transmitting means by means of a two-way communication line, and a display device for displaying the graph or table;

said measuring means includes a pair of first pressure sensors for individually detecting input pressures supplied to one end of the left-hand and right-hand filter cigarettes, a pair of second pressure sensors for individually detecting output pressures developing at the other end of the filter cigarettes, and computing means for computing the respective dilutions of the left-hand and right-hand filter cigarettes in accordance with a differential pressure between pressure signals delivered from the first and second pressure sensors, said computing means includes detecting means for detecting the speed of manufacture of the left-hand and right-hand filter cigarettes and first correcting means for correcting the measurement results in accordance with the manufacturing speed detected by the detecting means; and said computing means further includes second correcting means for correcting the measurement results in accordance with a brand of the cigarettes to be manufactured.

9. The system according to claim 8, wherein said first processing means includes a second memory device for storing the obtained quality data.

10. The system according to claim 9, wherein said second processing means includes means for manually or periodically giving a transmission command for the quality data to said first processing means.

\* \* \* \* \*